United States Patent [19]
Bobb

[11] Patent Number: 5,367,175
[45] Date of Patent: Nov. 22, 1994

[54] METHOD OF MEASURING LIQUID LEVEL WITH A THERMAL INTERFACE DETECTION

[75] Inventor: Lloyd C. Bobb, Horsham, Pa.

[73] Assignee: The United States of America as represented by the Secretary of the Navy, Washington, D.C.

[21] Appl. No.: 159,962

[22] Filed: Nov. 24, 1993

[51] Int. Cl.⁵ ............................................. G01N 15/06
[52] U.S. Cl. ............................ 250/577; 250/227.14; 250/904; 73/293
[58] Field of Search ............. 250/577, 227.14, 227.19, 250/227.24, 904; 73/293, 292

[56] References Cited

U.S. PATENT DOCUMENTS

| | | | |
|---|---|---|---|
| 4,287,427 | 9/1981 | Scifres | 250/577 |
| 4,891,512 | 1/1990 | Naden | 250/227.14 |
| 5,047,626 | 9/1991 | Bobb et al. | 250/227.19 |
| 5,115,127 | 5/1992 | Bobb et al. | 250/227.19 |
| 5,166,988 | 11/1992 | Bobb et al. | 385/1 |

Primary Examiner—David C. Nelms
Assistant Examiner—Que T. Le
Attorney, Agent, or Firm—James V. Tura; James B. Bechtel; Susan E. Verona

[57] ABSTRACT

A method of measuring the position of a liquid surface within a vessel is described. An optical fiber is provided which has first and second ends and has an energy-absorbing element of a predetermined length disposed upon a portion of the cladding thereof such that there is a thermal interface between the energy-absorbing element and the cladding. The optical fiber is then positioned in the vessel so that the energy-absorbing element disposed thereon extends a known distance into the vessel along a known depth gradient of the vessel and so that the energy-absorbing element will intersect the liquid surface over the anticipated range of positions thereof. Single-frequency, coherent light is then transmitted through the core of the optical fiber by launching it into the first end of the optical fiber. A pulse of energy is applied across the entire length of the energy-absorbing element to heat it, and then the transmitted light is received from the second end of the optical fiber. The change in phase of the transmitted light resulting from applying the pulse of energy is then measured, and the position of the liquid surface is then determined in accordance with the change in phase.

14 Claims, 4 Drawing Sheets

METHOD OF MEASURING LIQUID LEVEL WITH A THERMAL INTERFACE DETECTION

STATEMENT OF GOVERNMENT INTEREST

The invention described herein may be manufactured and used by and for the Government of the United States of America for governmental purposes without the payment of any royalties thereon or therefor.

BACKGROUND OF THE INVENTION

The present invention relates generally to a method of measuring the position of a liquid surface within a vessel, and more particularly to a method of measuring liquid level using an optical fiber sensor.

There are a variety of methods of measuring liquid level, the most commonly-used non-fiber-optic methods being based on such physical phenomena as buoyancy, capacitance, ultrasonic waves, and pressure transmission.

Liquid level sensors based on buoyancy employ a buoyant float which moves with changing liquid level. A mechanical linkage or magnetic couple translates the float's up-and-down motion into a motion of a contact which is either open or closed, indicating whether the liquid level is above or below a specific level. Accuracy is typically limited to approximately a quarter of an inch.

In the capacitance approach to measuring liquid level, an electrode is installed in the vessel and the capacitance between this electrode and the wall of the vessel is measured. Air has a dielectric constant of one and the liquid has a greater dielectric constant. As the tank fills with the liquid, the dielectric constant rises and therefore so does the capacitance. Therefore, a measure of the capacitance of the vessel is an indication of the amount of liquid present. Any change in the dielectric constant of the liquid will cause an incorrect reading.

Ultrasonic techniques sense liquid level by measuring the time it takes for a pulsed high-frequency sound wave to travel from a transducer downward through the air at the top of the vessel, reflect off the surface of the liquid and return to the sensor. Accuracy is typically limited to about 0.25% of the full-scale reading. Ultrasonic sensors are not reliable in the presence of surface foam, and their functioning may be impaired by falling liquids, steam, and dense vapors and dust in the vessel.

Liquid level sensors based on pressure operate on the principle that the pressure at the sensor increases directly with the depth of the water above it. One such sensor is called a bubbler. In a bubbler, compressed air is forced down a tube which runs to the bottom of the vessel at a pressure which will cause it to bubble out of the end of the tube. That pressure is an indication of the depth of the liquid above the end of the tube. One disadvantage of this sensor is that the end of the tube can become clogged by the liquid.

Optical fibers have been used in liquid level sensing. For example, point sensors work on the principle of total internal reflection. Light is sent down an optical fiber and the amount of light that gets reflected back from the end of that fiber depends on whether or not the fiber end is in the liquid or above it. They are also susceptible to contamination of the end of the fiber, and would not work in any kind of liquid that could stick to the end of the fiber. A variation of this type of sensor has a U-shaped fiber with the cladding stripped away from the U-shaped portion. When the U-shaped portion of the fiber is immersed in the liquid, and light is transmitted through the fiber, some of it is lost to the liquid. Therefore, the amount of light that is received depends on whether the U-shaped portion of the fiber is in or above the liquid. Both of these sensors have the limitation that they merely tell you whether the liquid level is above or below a specific level.

A differential absorption optical fiber liquid level sensor uses a two-wavelength ratiometric approach to cancel out errors arising from variations in fuel characteristics and tank vibrations. It uses inexpensive LED sources and a multimode optical fiber and can have a 2-mm resolution over an 18-cm range. The sensor also has the advantage that only a transparent window is needed to look up through the liquid to measure the transmission through the liquid, making the method non-contact and therefore not subject to surface contamination or surface wetting of the optical surfaces. A disadvantage of this sensor is that if the absorption characteristics of the liquid are temperature-dependent, then the reading must be adjusted for that property. Of course, it will not work on liquids which do not transmit light.

Another optical fiber sensor is based on the continuation of the transmission through a bent fiber. Fibers formed with reversed curvatures of decreasing radii will induce an increasing amount of lower-mode light loss to the cladding as the light propagates along the multimode fiber. The sensor is arranged in the fluid in a vertical orientation so that the light travels along the fiber from the bottom or low point of the fluid to the top or the full point. As the fluid covers increasing lengths of the exposed fiber, it strips ever more power from the cladding. Data taken with this sensor show a monotonic decrease of output intensity as a function of increasing fluid level. This sensor has an accuracy of a few centimeters.

Crosstalk between two multimode optical fibers has also been used to sense liquid level. The cladding is removed from a portion of each of the fibers to expose their cores, and then they are aligned so that the exposed cores are adjacent to each other. Light is propagated through one the fibers. When liquid is present in the region between the cores light will couple from the one fiber into the other. This sensor is very accurate over a limited range. The disadvantages are that it is very susceptible to contamination and it will only work with a limited range of liquids which have the right index of refraction. Also, the amount of coupling changes as the index of refraction changes, which happens with temperature, requiring that the sensor be temperature-compensated.

A digital optical fiber liquid level sensor operates on the selective coupling at the liquid surface between a source waveguide and an array of digitally masked receiving waveguides. The receiving waveguides carry optical high-low signals to a remote detector in a discriminator circuit. This sensor is capable of liquid level resolution to several millimeters and it can operate over a total range of liquid levels of several meters. This sensor also depends on the index of refraction of the medium.

A high-precision remote liquid level measurement can be made using a combination of optical radar and optical fibers. This technique is similar to the ultrasonic technique in which liquid level is measured by measuring the length of time it takes for radiation to travel the distance from the source to the surface and back to a detector. This distance measurement is made using the technique of optical radar in which the phase of an amplitude-modulated lightwave reflected from a remote target is compared with that of the original phase of the launched beam. This technique enables measurements to be made ranging from 0.1 m to 5 m with an accuracy of about 1 mm throughout the range. This system has all the advantages of the non-contact techniques that were described previously. Its readings are adversely affected by foam and the presence of particles or droplets between the source and the surface that would cause reflections.

It can be seen that a need exists for a highly accurate, depth-continuous method of measuring liquid level which can be used in a corrosive environment, has no moving parts within the liquid-containing vessel, can be used with a variety of liquids, is insensitive to such liquid properties as index of refraction, dielectric constant, absorption characteristics, and light transmissivity, operates in the presence of foam and various contaminants, and functions even when the liquid surface is not horizontal

SUMMARY OF THE INVENTION

It is a general object of the present invention to provide a method of measuring the position of a liquid surface in a vessel.

It is a more specific object of the present invention to provide a highly accurate method of measuring liquid level using an optical fiber.

It is yet another object of the present invention to provide a method of measuring the position of a liquid surface in a vessel, which method is depth-continuous and does not depend on gravity to function and can therefore measure the position of a liquid surface in a vessel even when the surface is not horizontal, as in a syringe.

It is still another object to provide a method of measuring liquid level which can be used in a corrosive environment and can function in the presence of foam and various contaminants.

It is also an object of the present invention to provide such a method which operates independently of such characteristics of the liquid as its dielectric constant, its absorption characteristics, its light transmissibility, and its index of refraction.

These and other objects are accomplished by a method of measuring the position of a liquid surface within a vessel, in which an optical fiber is provided which has first and second ends and has an energy-absorbing element of a predetermined length disposed upon a portion of the cladding thereof such that there is a thermal interface between the energy-absorbing element and the cladding. The optical fiber is then positioned in the vessel so that the energy-absorbing element disposed thereon extends a known distance into the vessel along a known depth gradient of the vessel and so that the energy-absorbing element will intersect the liquid surface over the anticipated range of positions thereof. Single-frequency, coherent light is then transmitted through the core of the optical fiber by launching it into the first end of the optical fiber. A pulse of energy is applied across the entire length of the energy-absorbing element to heat it, and then the transmitted light is received from the second end of the optical fiber. The change in phase of the transmitted light resulting from applying the pulse of energy is then measured, and the position of the liquid surface is then determined in accordance with the change in phase.

Other objects, advantages, and novel features of the invention will become apparent from the following detailed description of the invention when considered in conjunction with the accompanying drawings.

DESCRIPTION OF THE PREFERRED EMBODIMENT

Figure 1:
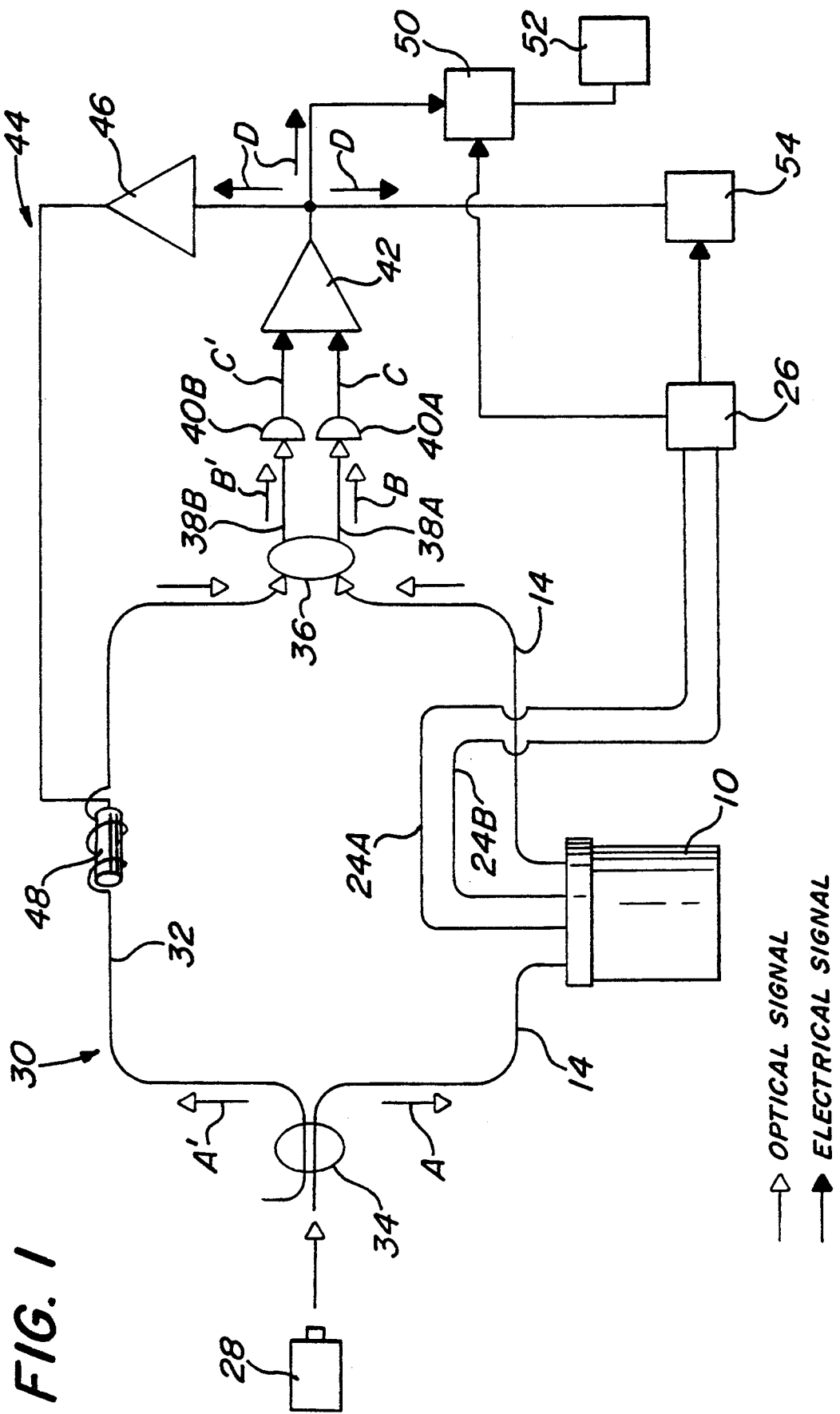
FIG. 1 is a schematic representation of apparatus for use in the liquid-level measuring method of the present invention.

Referring now to the drawings wherein like characters designate like or corresponding parts throughout the several views, there is shown in FIG. 1 a schematic diagram of a configuration for carrying out the method of the present invention. A vessel 10, shown in more detail in schematic FIG. 2, containing liquid 12 of unknown depth (including the possibility of being empty) has an optical fiber 14 positioned to extend therein. Optical fiber 14, which is preferably a single-mode optical fiber for propagating coherent, single-frequency light therethrough, has a core through which the light can propagate, a cladding and a non-stripping jacket.

Optical fiber 14 has disposed thereon an energy-absorbing element 16 of a known, predetermined length based on the range of anticipated liquid levels. Energy-absorbing element 16 is disposed on the cladding such that there is a thermal interface therebetween. The jacket is preferably removed from the portion of the cladding which has element 16 disposed thereon for this purpose. In the embodiment shown in FIGS. 1 and 2, energy-absorbing element 16 is a thin layer formed of a conductive material such as gold for absorbing electrical energy. Keeping the thermal mass of element 16 to a minimum saves energy and shortens the thermal response time; therefore, element 16 should preferably be a thin coating (on the order of 1000 angstroms or 0.1 micron thick) of the kind achievable using vacuum deposition, chemical vapor deposition, or sputtering. The gold layer may surround the entire circumference along a length of optical fiber 14. Element 16 may be overcoated with a thin plastic layer to isolate the element from the liquid or gas, if desired.

Figure 2:
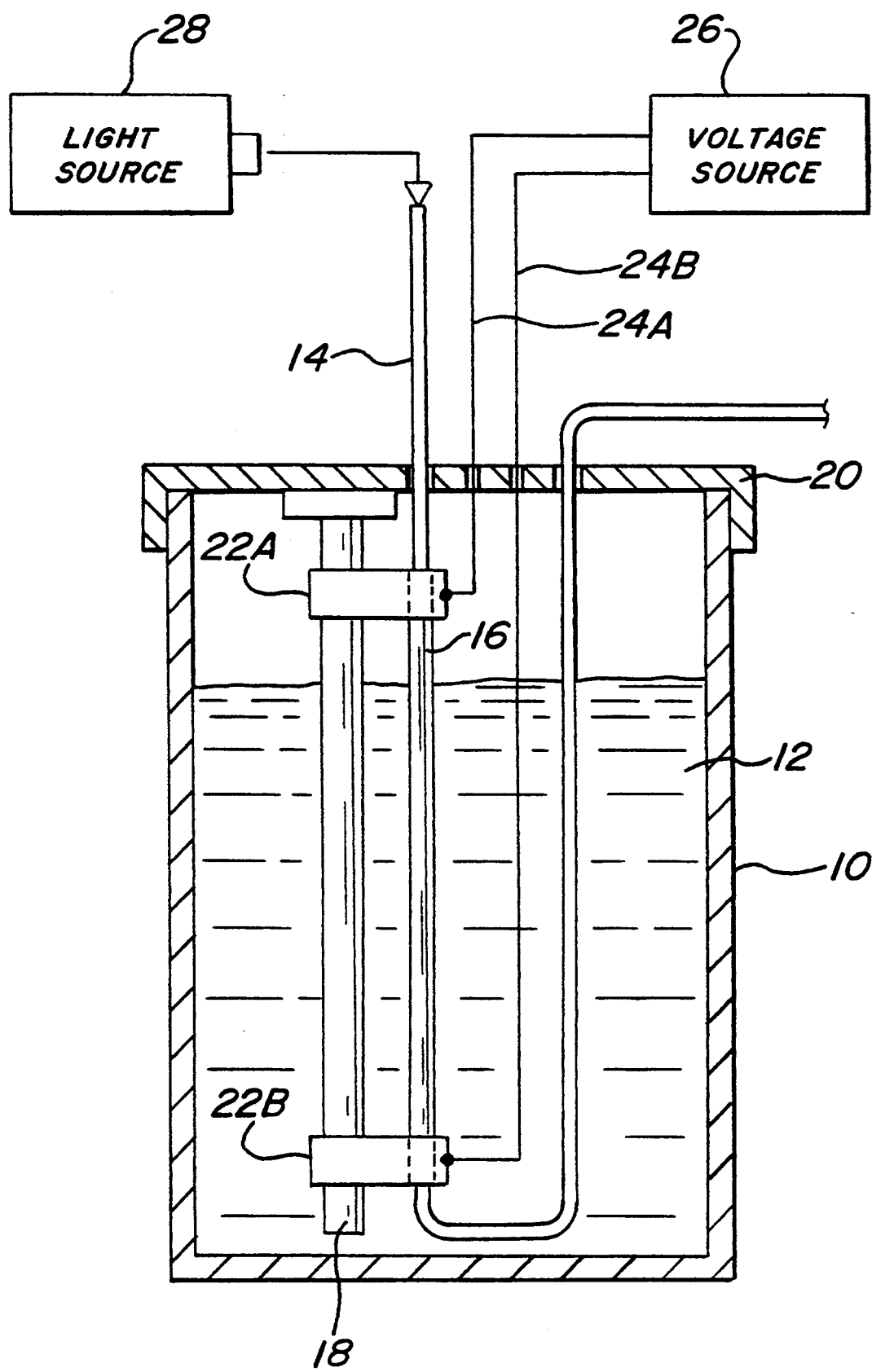
FIG. 2 is a more-detailed schematic representation of the vessel shown in FIG. 1.

Optical fiber 14 is positioned in vessel 10 so that energy-absorbing element 16 extends a known distance into the vessel along a known depth gradient of the vessel. Optical fiber 14 should be positioned so that energy-absorbing element 16 will intersect the liquid surface over the range of anticipated positions thereof. If an empty reading is to be measurable, element 16 should extend to the bottom of vessel 10. This positioning may be accomplished as shown in FIG. 2, with a rod 18 made of non-conductive material such as delrin or fiberglass and sized to be long enough to span the range of anticipated positions of the liquid surface. Rod 18 is positioned accordingly, and along a known depth gradient, preferably perpendicular to the surface, and may be held in place by being fixed at one end thereof to a lid 20 on vessel 10. Rod 18 has two fasteners 22a and 22b of conductive material such as copper fixed thereto for holding optical fiber 14 in an extended and straight position parallel thereto, but not in contact therewith. Fasteners 22a and 22b are fixed, for example by conductive epoxy or low-temperature solder, to energy-absorbing element 16 at each of its two ends, and act as electrical contacts for conducting electricity thereto via fastener wires 24a and 24b. Lid 20 has holes appropriately positioned for passage therethrough of optical fiber 14 and fastener wires 24a and 24b.

A pulsed voltage source 26 is electrically connected via wires 24a and 24b to fasteners 22a and 22b to supply a series of electrical pulses of a given energy level and known short duration to energy-absorbing element 16 along its entire length, to repeatedly momentarily heat it. Some of this heat transfers to optical fiber 14, and some transfers to the surrounding medium. More heat transfers to the surrounding medium when the medium is liquid than when the medium is gas, and when more heat transfers to the surrounding medium, less heat transfers to optical fiber 14. Therefore, when the surrounding medium is liquid, less heat transfers to optical fiber 14 than when the surrounding medium is gas. The amount of heat transferring to optical fiber 14 is thus proportional to the amount of gas surrounding element 16. Therefore, by measuring the amount of heat transferring to optical fiber 14, one can determine the relative amounts of liquid and gas that are surrounding element 16, thereby allowing one to measure the relative position of the liquid surface or liquid level.

Heat transferred to the fiber heats the fiber's core. One can measure the amount of heat transferring to the core of optical fiber 14 by launching coherent, single-frequency light from a coherent light source 28, such as a single-frequency helium-neon laser, into one end of the optical fiber so that it propagates through the core thereof, and measuring the change in phase of the light which occurs as a result of the optical fiber being heated. The phase of the light propagating through an optical fiber of length L is given by $\phi = 2\pi nL/\lambda$ where n is the effective refractive index, which may be approximated by the refractive index of the core of the optical fiber, and $\lambda$ is the wavelength of the light in free space. A change in the optical fiber's temperature T (as in when it is heated) results in a proportionate phase shift $\Delta\phi$ of the light in the optical fiber because of the temperature-induced change in the refractive index n of the core of the optical fiber, the change in the length L of the waveguide due to thermal expansion, and the photoelastic effect.

The change in phase of the light can be measured by using any of a variety of optical fiber interferometers. A two-fiber interferometer such as a Mach-Zehnder interferometer 30, for example, may be used to observe the interference which occurs between the light propagating through optical fiber 14 and light from the same source 28 which propagates through a reference optical fiber 32, which is unaffected by the temperature change. Coherent light source 28 is coupled through a beam splitter 34, such as an optical fiber coupler, to launch substantially identical light beams A and A' through the cores of optical fiber 14 and reference optical fiber 32, which forms the other arm of interferometer 30. The light beams A and A' from optical fibers 14 and 32 are combined to interfere at a combiner 36, such as an optical fiber coupler. The combined light then exits combiner 36 as two beams B and B' via exit optical fibers 38a and 38b to be collected by photodiodes 40a and 40b which convert the light beams B and B' to electrical signals C and C' which are proportional to the intensities of beams B and B'. A differential amplifier 42 receives and compares electrical signals C and C' from photodiodes 40a and 40b and produces an electrical signal D which is proportional to the difference in intensities of beams B and B' through exit optical fibers 38a and 38b. The difference in intensities of beams B and B' is indicative of the relative phase of the beams A and A' through optical fibers 14 and 32. Signal D therefore indicates the phase shift which has occurred as a result of optical fiber 14 being heated by the energy pulses.

Signal D from differential amplifier 42 is applied to a quadrature-maintaining means 44 such as a locking amplifier 46 connected to a PZT fiber stretcher 48 to lock interferometer 30 in quadrature. Other quadrature-maintaining means may be used as well. Quadrature-maintaining means 44 should have a response time which is fast enough to compensate for room temperature variations yet slow enough that the short heating pulse is not compensated for.

Interferometer 30 should be operated in the region in which there is a linear relationship between the fiber core's temperature and the output signal D. This region is within an eighth of a fringe of quadrature. To keep interferometer 30 operating in this region, the amount of temperature-rise of the fiber's core must be controlled, which is accomplished by controlling the energy in the heating pulse. The voltage level of pulsed voltage source 26 should be adjusted until the desired fringe shift is obtained. The appropriate voltage level will depend on the resistance of energy-absorbing element 16, which in turn is based on the particular conductive material chosen, its thickness, and its length. The duration of the heating pulse should be less than the thermal response time of the fiber, which is the time required for heat applied to the outer surface of the fiber to reach the core, and is an inherent characteristic of the fiber. A pulse duration of less than 1 msec is preferred. The delay between pulses should be long enough to allow interferometer 30 to return to quadrature.

Signal D from differential amplifier 42 is also recorded and stored by a signal analyzer 50, which may be, for example, an HP 3651A Signal Analyzer. Pulsed voltage source 26 provides a trigger pulse to signal analyzer 50 to signal it to record a waveform for each heating pulse applied to optical fiber 14. Signal analyzer 50 captures and stores each waveform and then may average them in groups of approximately 50 to reduce significantly the background noise, if desired. Output from signal analyzer 50 is then plotted by a plotter 52. Signal D from differential amplifier 42 is also sent to an oscilloscope 54 which is also triggered by pulsed voltage source 26 for displaying each individual waveform.

It is convenient to use the peak temperature reached by the core of optical fiber 14 for each pulse (or group of pulses if averaging), which correlates to the peak of the corresponding waveform, as the value to correlate with the liquid level. Of course, plotter 52 may be set to plot only the peak values, which can be calibrated to represent liquid level.

Figure 3:
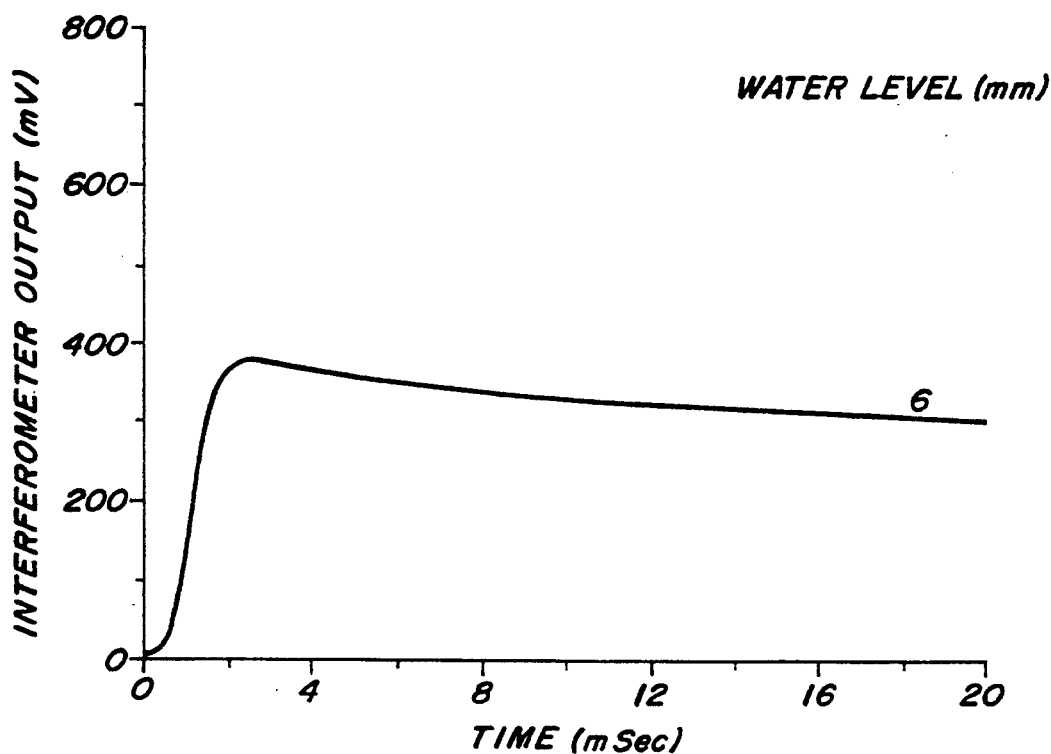
FIG. 3 is a plot of the output of the interferometer of FIG. 1 versus time for a given fixed liquid level, averaged over approximately 50 heating pulses of the optical fiber.
Figure 4:
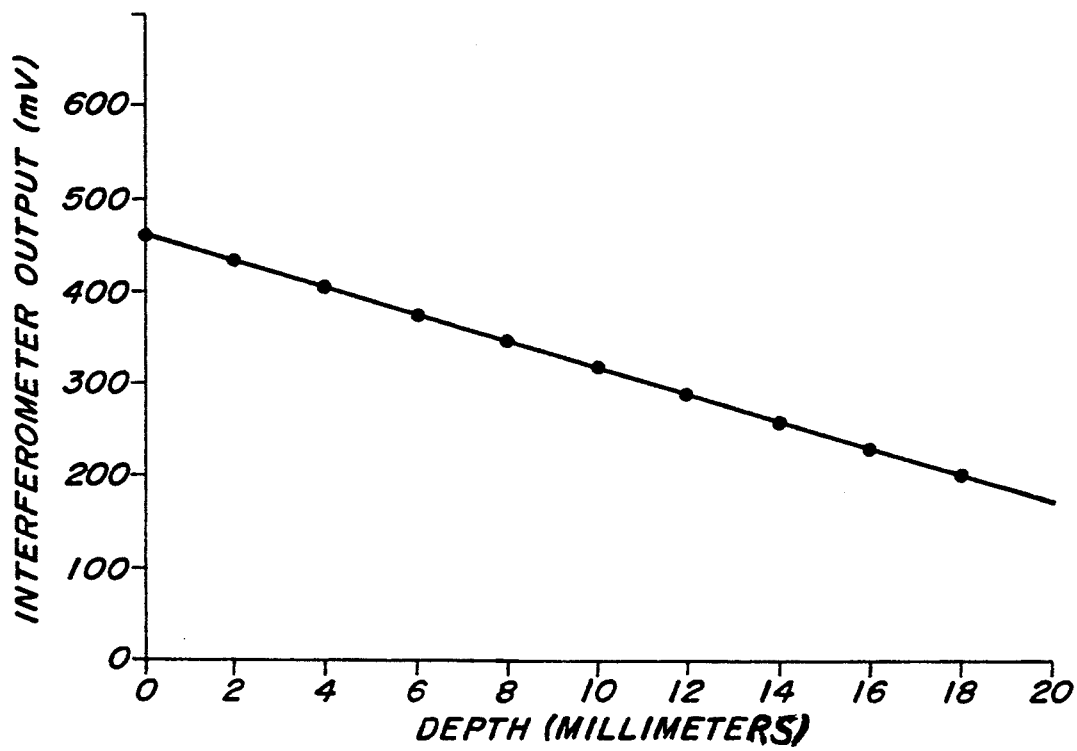
FIG. 4 is a plot of the average peak interferometer output versus time for a range of liquid levels measured according to the present invention.

The method of the present invention was demonstrated using as optical fiber 14 an ITT Type T-1601 single-mode optical fiber having a four-micron diameter silica core, a forty-micron outside diameter $B_2O_3$-doped silica cladding, and an eighty-five micron outside diameter silica substrate. A one-inch section of the optical fiber had disposed thereon a gold coating 1000 angstroms thick with a resistance of 11.7 ohms. The optical fiber was immersed in water the depth of which was varied. Pulsed voltage source 26 applied an electrical pulse of 1.4 volts and one millisecond in duration to the gold coating via electrically conductive fasteners 22a and 22b. Quadrature-maintaining means 44 had a response time of several hundred milliseconds, so that the one-millisecond heating pulses were not phase-compensated. A Mach-Zehnder interferometer was used. One resulting waveform representing an average of 50 waveforms from plotter 52 is shown in FIG. 3 for a water level of 6 mm. A plot of the peak signal (mV) vs. water level (mm) for a series of heating pulses and water levels is given in FIG. 4. From this plot the water level was determinable to within less than 1 mm.

Figure 5:
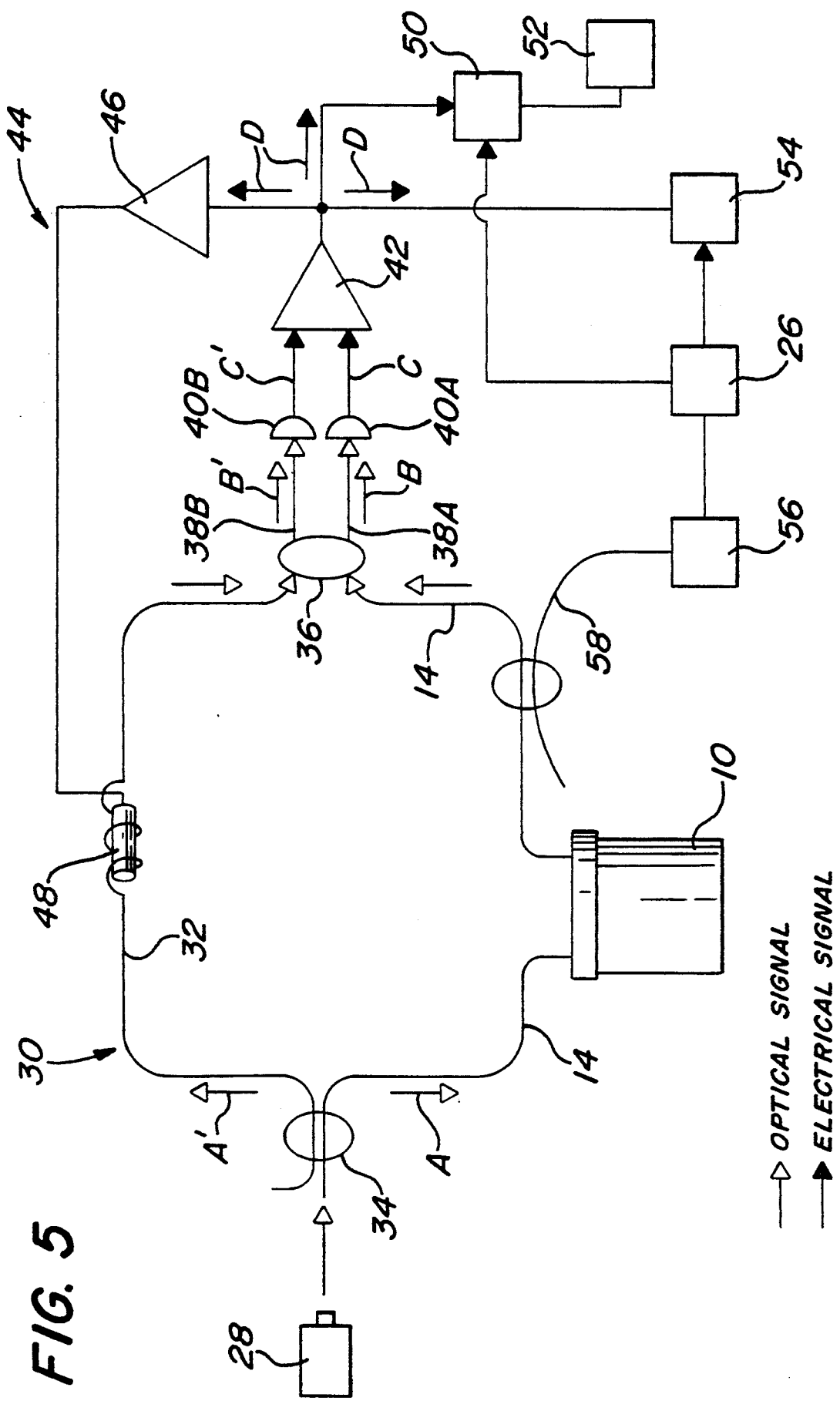
FIG. 5 is a schematic representation of apparatus for use in an alternate embodiment of the liquid-level measuring method of the present invention.

In another embodiment, shown in FIG. 5, energy-absorbing element 16 is a light-absorbing element. Pulsed voltage source 26 provides voltage to a light energy source 56, such as a laser diode, which provides a pulse of light energy to energy-absorbing element 16. Light-absorbing element 16 may be composed of any material which is capable of absorbing a preselected wavelength band of light and generating heat in response thereto and which is capable of thermally interfacing with optical fiber 14, either on or within the cladding. Thin metallic films such as gold, known absorbers such as carbon black, and even pigment, as from a water-proof marking pen, are effective materials for disposing on the cladding. The amount of the circumference of the cladding which is covered by light-absorbing element 16 may vary. One convenient embodiment is to dispose light-absorbing element 16 around the entire circumference of the cladding. Energy-absorbing element 16 may be overcoated with gold or any other inert material to protect it from the liquid, if desired.

Alternatively, light-absorbing element 16 may be diffused into the cladding of optical fiber 14 around the entire circumference thereof. In this embodiment, light-absorbing element 16 may be any of a variety of metal atoms which are absorbers and which are capable of being diffused into glass, such as neodymium. As with the coating embodiment, the circumferential amount of cladding which is diffused with light-absorbing material may vary.

Pulsed voltage source 26 supplies pulses of electrical energy to light energy source 56, which is coupled to launch pulses of light into the cladding of optical fiber 14 in the direction of element 16 via a multimode fiber 58. Pulsed voltage source 26 also provides trigger pulses to signal analyzer 50 and oscilloscope 54, as in the previous embodiment. The location on optical fiber 14 where light is coupled into the cladding should be between light-absorbing element 16 and photodiodes 40a and 40b so that light from source 56 propagates through the cladding in a direction which is away from the photodiodes. Those skilled in the optical arts are aware of means for coupling light into the cladding of a fiber so that it will remain in the cladding only and propagate in the desired direction. One technique is to fix multimode fiber 58 to optical fiber 14 along a small portion of the length of each, oriented in such a way that the light, when coupled into the cladding, will continue to propagate in the same direction, towards element 16. Multimode fiber 58 may be fixed to optical fiber 14 by removing the cladding from a portion of the multimode fiber and bonding that portion to a portion of the optical fiber from which the jacket has been removed. Bonding can be achieved either with index gel, or by fusing the portions together with heat while stretching multimode fiber 58 and optical fiber 14. To ensure that the light launched into the cladding reaches light-absorbing element 16 without being stripped away enroute, the jacket should be made of a material, such as silicone resin, which has a lower index of refraction than the cladding.

The wavelength band of light energy source 56 must be one which is readily transmitted by multimode fiber 58 and optical fiber 14. A constant amount of light energy should preferably be deposited per unit length of light-absorbing element 16. This can be achieved by tailoring the absorption profile or attenuation length of element 16, by increasing the amount of surface area of the cladding which has light-absorbing element 16 disposed thereon with increasing distance from the point where light is coupled into the cladding. Alternatively, the wavelength bands of light energy source 56 and element 16 can be selected so that only a small portion of the light power which reaches the element is absorbed thereby. In this case, the power of the light propagating through the cladding does not drop off significantly as it proceeds through the portion having element 16 connected thereto.

The energy of the heating pulse is controlled by adjusting the voltage level of pulsed voltage source 26 and the energy output of light energy source 56 until the desired fringe shift is obtained, as discussed in connection with the previous embodiment. The appropriate energy output of light energy source 56 will be based on the absorption characteristics of the particular material used for the energy-absorbing element. The duration of the heating pulse should be less than the thermal response time of the fiber, preferably 1 msec or less. In all other respects this embodiment is the same as the previously-described embodiment.

Some of the many advantages of the present invention should now be readily apparent. For instance, a highly accurate method of measuring the position of a liquid surface in a vessel has been provided. Furthermore, the method is depth-continuous and does not depend on gravity to function, allowing one to measure the position of a liquid surface in a vessel even when the surface is not horizontal. The method also operates independently of such characteristics of the liquid as its dielectric constant, its absorption characteristics, its light transmissibility, and its index of refraction. Additionally, the method can be used in a corrosive environment and at elevated temperatures and pressures. Finally, there are no moving parts within the liquid-containing vessel.

Those skilled in the art will appreciate without any further explanation that many modifications and variations are possible to the above disclosed method of measuring liquid level, within the concept of this invention. Consequently, it should be understood that all such modifications and variations fall within the scope of the following claims.

What is claimed is:

1. A method of measuring the position of a liquid surface within a vessel, comprising the steps of:
    providing an optical fiber having first and second ends and having an energy-absorbing element of a predetermined length disposed upon a portion of the cladding thereof such that there is a thermal interface between the energy absorbing element and the cladding;
    positioning the optical fiber in the vessel so that the energy absorbing element disposed thereon extends a known distance into the vessel along a known depth gradient of the vessel and so that the energy-absorbing element will intersect the liquid surface over the anticipated range of positions thereof;
    transmitting single-frequency, coherent light through the core of the optical fiber by launching the light into the first end of the optical fiber;
    applying a pulse of energy across the entire length of the energy-absorbing element to heat it;
    receiving the transmitted light from the second end of the optical fiber;
    measuring the change in phase of the transmitted light resulting from applying the pulse of energy; and
    determining the position of the liquid surface in accordance with the change in phase.

2. The method of claim 1, wherein the energy-absorbing element is composed of a conductive material, and the pulse of energy applied to the energy-absorbing element is electrical energy.

3. The method of claim 2, wherein the pulse of electrical energy is applied to the energy-absorbing element by a voltage source electrically connected to electrodes at each end of the energy-absorbing element.

4. The method of claim 1, wherein the energy-absorbing element is a light-absorbing material, and the pulse of energy applied to the energy-absorbing element is light energy.

5. The method of claim 4, wherein the pulse of light energy is applied to the energy-absorbing element by launching light down the cladding of the optical fiber towards the energy-absorbing element.

6. The method of claim 4, wherein the energy-absorbing element is disposed upon the outer surface of a portion of the cladding of the optical fiber.

7. The method of claim 4, wherein the energy-absorbing element is disposed within the cladding of the optical fiber.

8. The method of claim 1, wherein the known depth gradient of the vessel is transverse to the liquid surface.

9. The method of claim 1, wherein said step of measuring the change in phase of the transmitted light resulting from applying the pulse of energy further comprises the step of monitoring the signal output of an interferometer which is maintained in quadrature in which the optical fiber having the energy-absorbing element disposed thereon forms an arm thereof.

10. The method of claim 9, wherein the interferometer is operated within an eighth of a fringe of quadrature.

11. The method of claim 9, wherein the duration of the pulse of energy applied across the entire length of the energy-absorbing element is less than the response time of the optical fiber.

12. The method of claim 11, wherein said step of monitoring the signal output of an interferometer which is maintained in quadrature further comprises the step of monitoring the signal output of the interferometer from the time the pulse of energy is applied until the interferometer returns to quadrature, to form a signal output waveform.

13. The method of claim 12, further comprising the step of forming and averaging a plurality of signal output waveforms and producing an average signal output waveform.

14. The method of claim 12, wherein said step of determining the position of the liquid surface in accordance with the change in phase further comprises the step of correlating the signal output waveform to the fraction of the energy-absorbing element surrounded by the liquid.

* * * * *